(12) United States Patent
Kamada et al.

(10) Patent No.: US 9,719,957 B2
(45) Date of Patent: Aug. 1, 2017

(54) GAS SENSOR ELEMENT AND GAS SENSOR

(71) Applicant: NGK SPARK PLUG CO., LTD., Nagoya-shi, Aichi-ken (JP)

(72) Inventors: Kentaro Kamada, Komaki (JP); Masaki Nakagawa, Komaki (JP); Koji Shiotani, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 511 days.

(21) Appl. No.: 14/146,999

(22) Filed: Jan. 3, 2014

(65) Prior Publication Data

US 2014/0190828 A1 Jul. 10, 2014

(30) Foreign Application Priority Data

| Jan. 8, 2013 | (JP) | ................................. 2013-000999 |
| Feb. 26, 2013 | (JP) | ................................. 2013-035682 |
| Oct. 28, 2013 | (JP) | ................................. 2013-223457 |
| Nov. 8, 2013 | (JP) | ................................. 2013-231774 |

(51) Int. Cl.

| G01N 27/30 | (2006.01) |
| G01N 27/407 | (2006.01) |
| G01M 15/10 | (2006.01) |
| G01N 33/00 | (2006.01) |

(52) U.S. Cl.
CPC ...... *G01N 27/4071* (2013.01); *G01M 15/104* (2013.01); *G01N 27/4072* (2013.01); *G01N 27/4077* (2013.01); *G01N 27/4078* (2013.01); *G01N 33/0037* (2013.01)

(58) Field of Classification Search
CPC ... G01N 27/4071; G01N 27/407; G01N 27/30
See application file for complete search history.

(56) References Cited

U.S. PATENT DOCUMENTS

| 4,927,517 | A | * | 5/1990 | Mizutani | ............ | G01N 27/4065 |
| | | | | | | 204/406 |
| 5,989,624 | A | * | 11/1999 | Kida | .................. | G01N 27/4075 |
| | | | | | | 204/421 |
| 6,344,119 | B2 | | 2/2002 | Kato et al. | | |
| 2001/0008211 | A1 | | 7/2001 | Kato et al. | | |
| 2002/0017467 | A1 | * | 2/2002 | Ando | .................... | F01N 3/0842 |
| | | | | | | 205/781 |
| 2003/0201171 | A1 | * | 10/2003 | Nakagaki | ............... | B01D 53/32 |
| | | | | | | 204/290.01 |
| 2010/0225339 | A1 | * | 9/2010 | Fujita | .................. | G01N 27/407 |
| | | | | | | 324/699 |
| 2013/0032480 | A1 | * | 2/2013 | Ito | ........................ | G01N 27/406 |
| | | | | | | 204/424 |

FOREIGN PATENT DOCUMENTS

| JP | 4165652 B2 | 10/2008 |
| JP | 2009014706 A | * 1/2009 |
| JP | 2010-122187 A | 6/2010 |

* cited by examiner

*Primary Examiner* — Susan D Leong

(74) *Attorney, Agent, or Firm* — Sughrue Mion, PLLC

(57) ABSTRACT

A first electrode (133) has an exposure portion (133*b*) exposed to a second measuring chamber (160), and a connection portion (133*d*) which is disposed at a position not exposed to the second measuring chamber (160) and is connected to the first lead (137) and which is a portion of the first electrode (133) located most distant from the second measuring chamber (160). The entire connection portion (133*d*) is located in a region A1 which extends from the second measuring chamber (160) over a distance of 1.0 mm or less.

9 Claims, 10 Drawing Sheets

GAS SENSOR ELEMENT AND GAS SENSOR

TECHNICAL FIELD

The present invention relates to a gas sensor element, and to a gas sensor having the gas sensor element.

BACKGROUND ART

A conventionally known gas sensor is attached to an exhaust path of an internal combustion engine such as an automotive engine for detecting the concentration of NOx (nitrogen oxide) in exhaust gas (gas to be measured) (refer to Patent Documents 1 and 2). Patent Documents 1 and 2 describe a gas sensor element which partially constitutes the gas sensor and includes a plate-like solid electrolyte body having oxygen ion conductivity, a first electrode provided on the front or back surface of the solid electrolyte body, a first lead connected to the first electrode, a second electrode provided on the front or back surface of the solid electrolyte body, a measuring chamber (second chamber) which is disposed in opposition to the first electrode and into which gas to be measured is introduced, and a reference oxygen chamber disposed in opposition to the second electrode. The gas sensor element is configured such that, as a result of movement of oxygen ions stemming from NOx contained in the gas-to-be-measured introduced into the measuring chamber, from the measuring chamber to the reference oxygen chamber through the solid electrolyte body, a current corresponding to the concentration of oxygen stemming from the NOx flows between the first electrode and the second electrode.

According to Patent Documents 1 and 2, in order to ensure oxygen pumping performance, the first electrode is formed to be porous. As a result, the first electrode becomes oxygen-permeable. Meanwhile, in order to improve electrical conductivity, high density per unit area is desired; thus, the first lead is formed to be dense. As a result, the first lead becomes oxygen-impermeable.

PRIOR ART DOCUMENTS

Patent Documents

[Patent Document 1] Japanese Patent No. 4165652
[Patent Document 2] Japanese Patent Application Laid-Open (kokai) No. 2010-122187

SUMMARY OF THE INVENTION

Problems to be Solved by the Invention

Incidentally, FIG. 4 in Patent Document 1 shows the first electrode disposed within the measuring chamber (second chamber). Furthermore, FIG. 4 shows the first lead which is connected to the first electrode within the measuring chamber in such a manner as to overlap the first electrode.

However, the combination of the oxygen-permeable first electrode and the oxygen-impermeable first lead has involved risk of occurrence of the following problem. That portion (hereinafter, may be referred to as a connection portion) of the first electrode which overlaps the first lead may deteriorate in oxygen pumping performance, potentially resulting in deterioration in accuracy in detecting the concentration of $NO_x$ in gas to be measured.

In view of the above problem, it is conceived that a portion of the first electrode is extended to a position which is not exposed to the measuring chamber, so as to dispose the connection portion at a position not exposed to the measuring chamber (a position located externally of the measuring chamber). This can restrain "deterioration in accuracy in detecting the concentration of $NO_x$ in gas to be measured, as a result of deterioration in oxygen pumping performance stemming from disposition of the connection portion within the measuring chamber."

However, even though the connection portion is disposed at a position not exposed to the measuring chamber, risk of occurrence of the following problem has been involved. The above-mentioned gas sensor is required to perform the following control: before starting regular control for detecting the concentration of $NO_x$ in gas to be measured, a fixed current is applied between the first electrode and the second electrode for a fixed period of time for moving (pumping out) oxygen stagnating in the interior of the gas sensor element to the reference oxygen chamber through the measuring chamber. The reason for this requirement is to properly detect the concentration of $NO_x$ (the concentration of oxygen stemming from $NO_x$) in gas-to-be-measured introduced from outside without influence of oxygen stagnating in the interior of the gas sensor element (more specifically, in the interior of the measuring chamber and the first electrode).

However, the disposition of the connection portion of the first electrode at a position not exposed to the measuring chamber (a closed position) has involved risk of failure to quickly pump out oxygen stagnating in (adsorbed to) the connection portion. Thus, risk of occurrence of the following phenomenon has been involved: even after start of regular control for detecting the concentration of $NO_x$ in gas to be measured, much oxygen remains within the connection portion, and, during regular control, the residual oxygen moves into the measuring chamber little by little over time. Because of influence of such supply of the residual oxygen from the connection portion into the measuring chamber over a long period of time, there has been involved risk of consumption of a long period of time from start of control until stabilization of sensor outputs (current flowing between the first electrode and the second electrode as a result of movement of oxygen ions from the measuring chamber to the reference oxygen chamber through the solid electrolyte body, and $NO_x$ concentration corresponding to the current). That is, there has been involved risk of consumption of a long period of time until establishment of a condition in which the concentration of $NO_x$ in gas to be measured can be properly detected.

The present invention has been conceived in view of such current situation, and an object of the invention is to provide a gas sensor element which has an oxygen-permeable first electrode and an oxygen-impermeable first lead connected to the first electrode and which can enter a condition in which the concentration of $NO_x$ in gas to be measured can be properly detected, in a short period of time without deterioration in oxygen pumping performance of the first electrode, as well as a gas sensor having the gas sensor element.

Means for Solving the Problems

According to an aspect of the present invention, there is provided a gas sensor element comprising a plate-like solid electrolyte body having oxygen ion conductivity, an oxygen-permeable first electrode provided on a front or back surface of the solid electrolyte body, an oxygen-impermeable first lead connected to the first electrode, an oxygen-permeable second electrode provided on the front or back surface of the solid electrolyte body, and a measuring chamber which is disposed in opposition to the first electrode and into which gas to be measured is introduced, and configured such that oxygen ions stemming from $NO_x$ contained in the gas-to-be-measured introduced into the measuring chamber move from the measuring chamber to a destination located externally of the measuring chamber through the solid electrolyte body, whereby a current corresponding to the concentration of oxygen stemming from the $NO_x$ flows between the first electrode and the second electrode, wherein the first electrode has an exposure portion exposed to the measuring chamber, and a connection portion which is disposed at a position not exposed to the measuring chamber and is connected to the first lead and which is a portion of the first electrode located most distant from the measuring chamber, and the entire connection portion is located in a region which extends from the measuring chamber over a distance of 1.0 mm or less.

The gas sensor element mentioned above comprises the oxygen-permeable first electrode and the oxygen-impermeable first lead connected to the first electrode. The first electrode has the exposure portion exposed to the measuring chamber, and the connection portion connected to the first lead and disposed at a position not exposed to the measuring chamber (a position located externally of the measuring chamber). For connection to the first lead at a position located externally of the measuring chamber, the connection portion is formed through extension of the first electrode in a direction directed away from the measuring chamber; thus, the connection portion is a portion of the first electrode located most distant from the measuring chamber.

Conventionally, a thus-configured gas sensor element has involved risk of failure to quickly pump out oxygen stagnating in (adsorbed to) the connection portion. Thus, risk of occurrence of the following phenomenon has been involved: even after start of regular control for detecting the concentration of $NO_x$ in gas to be measured, much oxygen remains within the connection portion, and, during regular control, the residual oxygen moves into the measuring chamber little by little. Because of influence of the phenomenon, there has been involved risk of consumption of a long period of time from start of control until stabilization of sensor output. That is, there has been involved risk of consumption of a long period of time until establishment of a condition in which the concentration of $NO_x$ in gas to be measured can be properly detected.

By contrast, in the gas sensor element mentioned above, the entire connection portion is disposed in a region which extends from the measuring chamber over a distance of 1.0 mm or less. By virtue of this, oxygen stagnating in the connection portion can be quickly pumped out, whereby there can be reduced time from start of control until stabilization of sensor output. That is, in a short period of time, there can be established a condition in which the concentration of $NO_x$ in gas to be measured can be properly detected.

Furthermore, in the gas sensor element mentioned above, the first electrode is connected to the first lead at a position not exposed to the measuring chamber. Thus, in contrast to the invention of Patent Document 1 (Japanese Patent No. 4165652) mentioned above, there can be restrained "deterioration in accuracy in detecting the concentration of $NO_x$ in gas to be measured, as a result of deterioration in oxygen pumping performance stemming from disposition of the connection portion within the measuring chamber."

Examples of "destination" which is located externally of the measuring chamber and to which oxygen ions stemming from $NO_x$ move from the measuring chamber include an internal space of the gas sensor element different from the measuring chamber (e.g., a reference oxygen chamber to be described later, or another measuring chamber) and a space located externally of the gas sensor element (e.g., a space with which the gas sensor element is in contact and in which gas to be measured flows, or a space with which the gas sensor element is in contact and in which the air flows).

Furthermore, preferably, the gas sensor element mentioned above further comprises a reference oxygen chamber disposed in opposition to the second electrode, and is configured such that the destination located externally of the measuring chamber is the reference oxygen chamber.

That is, preferably, in a gas sensor element comprising a plate-like solid electrolyte body having oxygen ion conductivity, an oxygen-permeable first electrode provided on a front or back surface of the solid electrolyte body, an oxygen-impermeable first lead connected to the first electrode, an oxygen-permeable second electrode provided on the front or back surface of the solid electrolyte body, a measuring chamber which is disposed in opposition to the first electrode and into which gas to be measured is introduced, and a reference oxygen chamber disposed in opposition to the second electrode, and configured such that oxygen ions stemming from $NO_x$ contained in the gas-to-be-measured introduced into the measuring chamber move from the measuring chamber to the reference oxygen chamber through the solid electrolyte body, whereby a current corresponding to the concentration of oxygen stemming from the $NO_x$ flows between the first electrode and the second electrode, the first electrode has an exposure portion exposed to the measuring chamber, and a connection portion which is disposed at a position not exposed to the measuring chamber and is connected to the first lead and which is a portion of the first electrode located most distant from the measuring chamber, and the entire connection portion is located in a region which extends from the measuring chamber over a distance of 1.0 mm or less.

By use of the gas sensor element mentioned above, the concentration of $NO_x$ in gas to be measured can be properly detected.

Furthermore, preferably, either one of the gas sensor elements mentioned above further comprises an insulation layer formed on the front or back surface of the solid electrolyte body; in the gas sensor element, the first lead and a portion of the first electrode are formed on the insulation layer; the exposure portion of the first electrode includes a contact portion which is in contact with the solid electrolyte body through a through hole extending through the insulation layer; and the connection portion of the first electrode is connected to the first lead on the insulation layer.

In the gas sensor element mentioned above, the exposure portion of the first electrode (a portion of the first electrode exposed to the measuring chamber) has the contact portion which is in contact with the solid electrolyte body through a through hole in the insulation layer. Meanwhile, the first lead is formed on the insulation layer (thus, the first lead is in noncontact with the solid electrolyte body). The connection portion of the first electrode is connected to the first lead on the insulation layer. Therefore, in the gas sensor element mentioned above, the connection portion of the first electrode is disposed at a position not exposed to the measuring chamber and is in noncontact with the solid electrolyte body.

Thus, in the gas sensor element mentioned above, only the contact portion of the first electrode can actually function as a sensing portion, and an object of detection; i.e., $NO_x$ concentration, can be accurately detected. The first lead differs from the first electrode in electrical characteristics; therefore, in a configuration in which the first lead and the connection portion connected to the first lead are partially in contact with the solid electrolyte body, gas concentration may fail to be accurately detected.

According to another aspect of the present invention, there is provided a gas sensor element comprising a platelike solid electrolyte body having oxygen ion conductivity, an oxygen-permeable first electrode provided on a front or back surface of the solid electrolyte body, an oxygen-impermeable first lead connected to the first electrode, an oxygen-permeable second electrode provided on the front or back surface of the solid electrolyte body, and a measuring chamber which is disposed in opposition to the first electrode and into which gas to be measured is introduced, and configured such that oxygen ions stemming from $NO_x$ contained in the gas-to-be-measured introduced into the measuring chamber move from the measuring chamber to a destination located externally of the measuring chamber through the solid electrolyte body, whereby a current corresponding to the concentration of oxygen stemming from the $NO_x$ flows between the first electrode and the second electrode, wherein the first electrode is disposed within the measuring chamber; the gas sensor element further comprises an insulation layer formed on the front or back surface of the solid electrolyte body; the first lead and a portion of the first electrode are formed on the insulation layer; and the first electrode has a contact portion which is in contact with the solid electrolyte body through a through hole extending through the insulation layer and a connection portion connected to the first lead on the insulation layer within the measuring chamber.

The gas sensor element mentioned above comprises the oxygen-permeable first electrode and the oxygen-impermeable first lead connected to the first electrode. The entirety of the first electrode is disposed within the measuring chamber (the entire front or back surface of the first electrode is exposed to the measuring chamber). Furthermore, the connection portion is connected to the first lead within the measuring chamber.

Through employment of such a configuration, oxygen stagnating in the connection portion can be quickly pumped out, whereby there can be reduced time from start of control until stabilization of sensor output. That is, in a short period of time, there can be established a condition in which the concentration of $NO_x$ in gas to be measured can be properly detected.

Additionally, the connection portion of the first electrode is connected to the first lead on the insulation layer (and is thus in noncontact with the solid electrolyte body). Therefore, although the connection portion is disposed within the measuring chamber, the connection portion does not affect oxygen pumping performance of the first electrode (the connection portion does not cause deterioration in oxygen pumping performance of the first electrode). Thus, there can be restrained deterioration in accuracy in detecting the concentration of $NO_x$ in gas to be measured.

Furthermore, preferably, the gas sensor element mentioned above further comprises a reference oxygen chamber disposed in opposition to the second electrode, and is configured such that the destination located externally of the measuring chamber is the reference oxygen chamber.

That is, preferably, in a gas sensor element comprising a plate-like solid electrolyte body having oxygen ion conductivity, an oxygen-permeable first electrode provided on a front or back surface of the solid electrolyte body, an oxygen-impermeable first lead connected to the first electrode, an oxygen-permeable second electrode provided on the front or back surface of the solid electrolyte body, a measuring chamber which is disposed in opposition to the first electrode and into which gas to be measured is introduced, and a reference oxygen chamber disposed in opposition to the second electrode, and configured such that oxygen ions stemming from $NO_x$ contained in the gas-to-be-measured introduced into the measuring chamber move from the measuring chamber to the reference oxygen chamber through the solid electrolyte body, whereby a current corresponding to the concentration of oxygen stemming from the $NO_x$ flows between the first electrode and the second electrode, the first electrode is disposed within the measuring chamber; the gas sensor element further comprises an insulation layer formed on the front or back surface of the solid electrolyte body; the first lead and a portion of the first electrode are formed on the insulation layer; and the first electrode has a contact portion which is in contact with the solid electrolyte body through a through hole extending through the insulation layer, and a connection portion connected to the first lead on the insulation layer within the measuring chamber.

By use of the gas sensor element mentioned above, the concentration of $NO_x$ in gas to be measured can be properly detected.

According to a further aspect of the present invention, there is provided a gas sensor comprising any one of the gas sensor elements mentioned above.

The gas sensor comprises any one of the gas sensor elements mentioned above. Thus, the gas sensor can enter a condition in which the concentration of $NO_x$ in gas to be measured can be properly detected, in a short period of time without deterioration in oxygen pumping performance of the first electrode.

MODES FOR CARRYING OUT THE INVENTION

Embodiment

An embodiment of the present invention will next be described with reference to the drawings.

Figure 1:
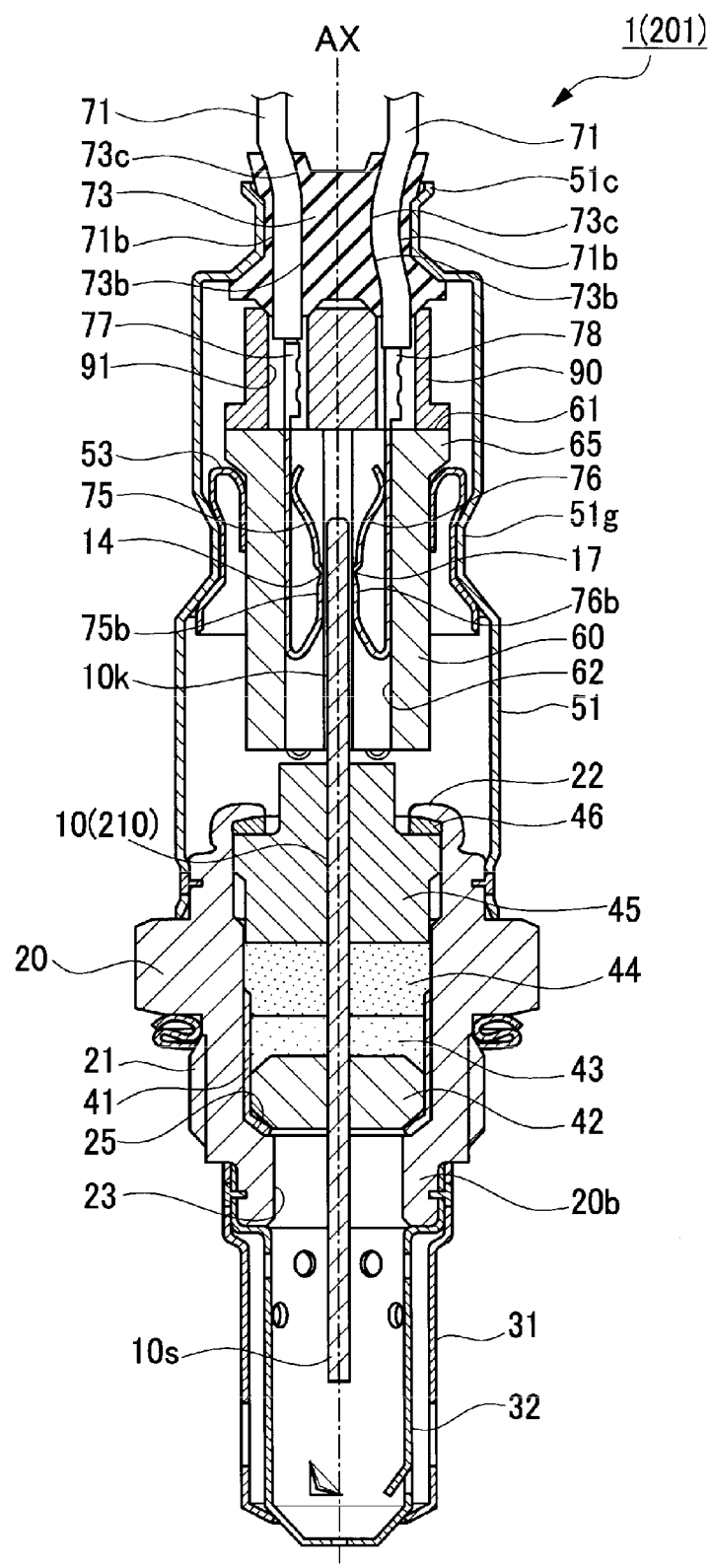
FIG. 1 Sectional view of a gas sensor according to an embodiment and a modified embodiment of the present invention.
Figure 2:
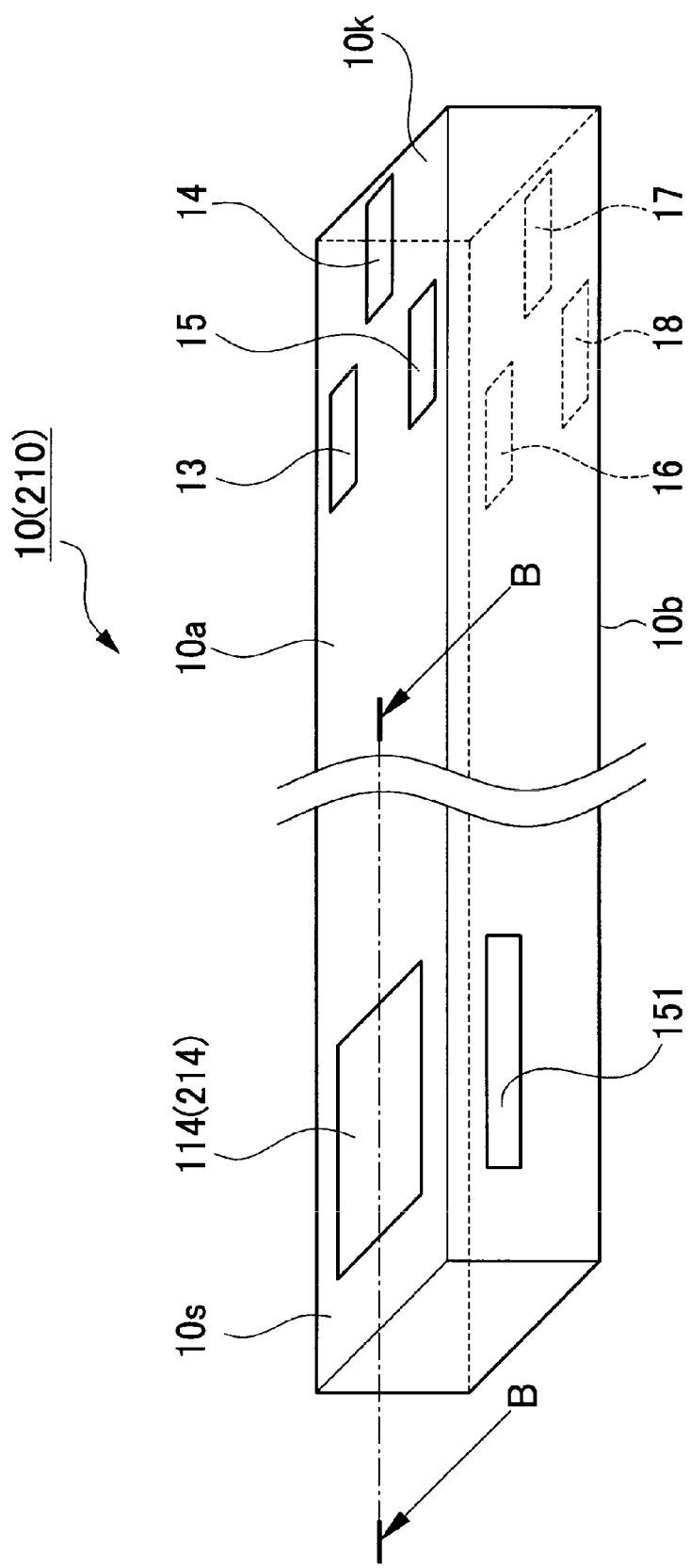
FIG. 2 Perspective view of a gas sensor element according to the embodiment and the modified embodiment.
Figure 3:
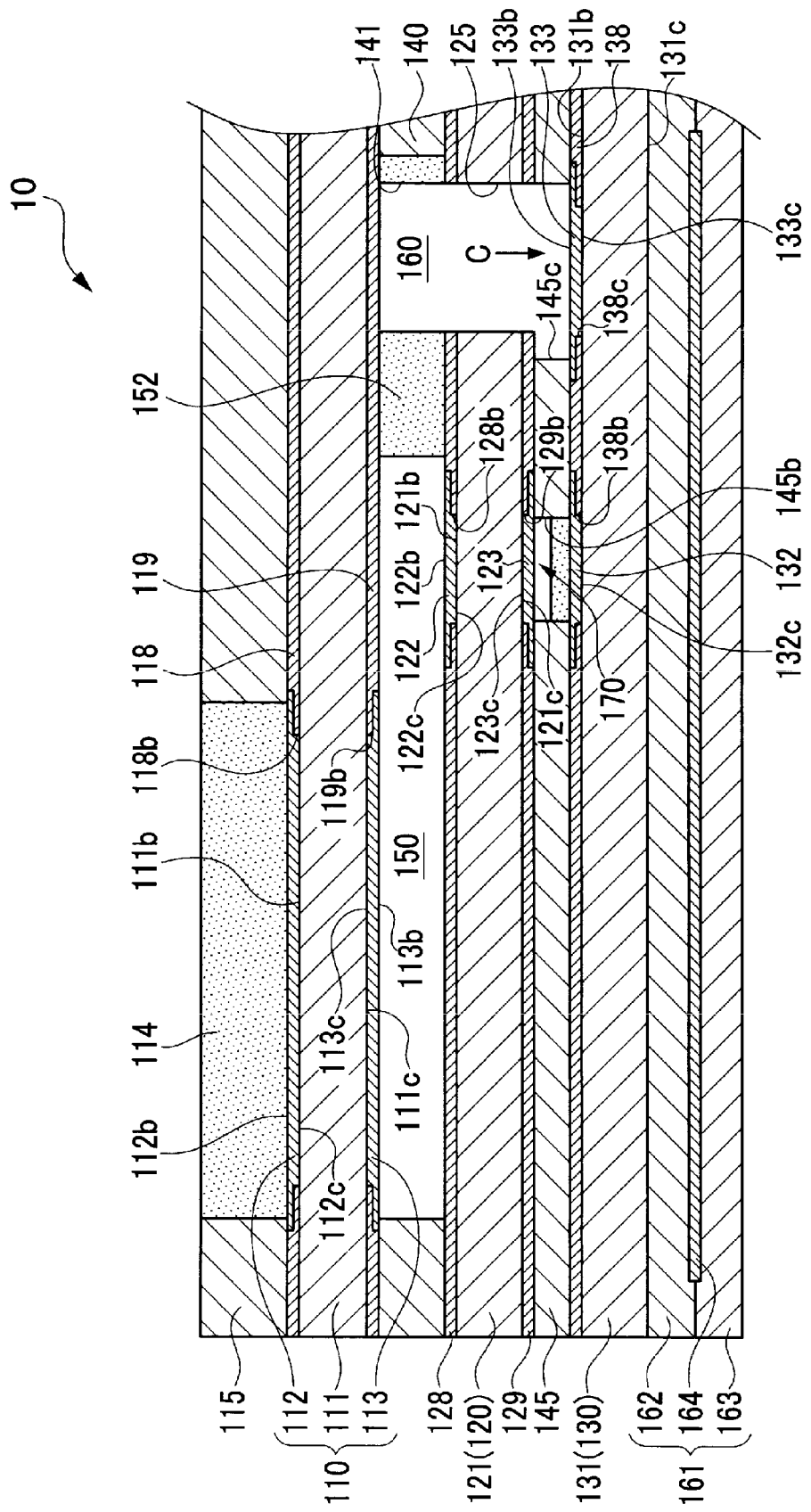
FIG. 3 Sectional view taken along line B-B of FIG. 2.
Figure 4:
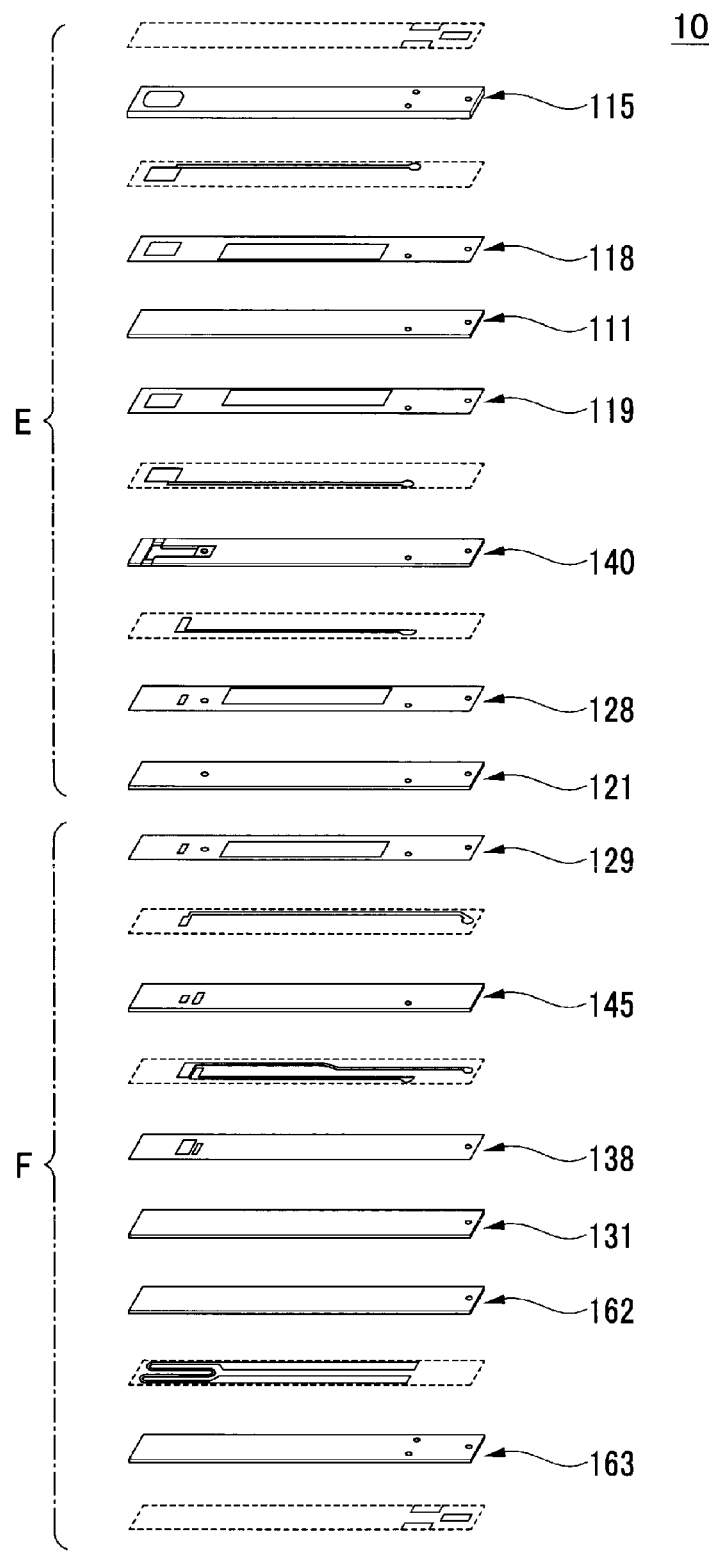
FIG. 4 Perspective view showing component layers of the gas sensor element.
Figure 5:
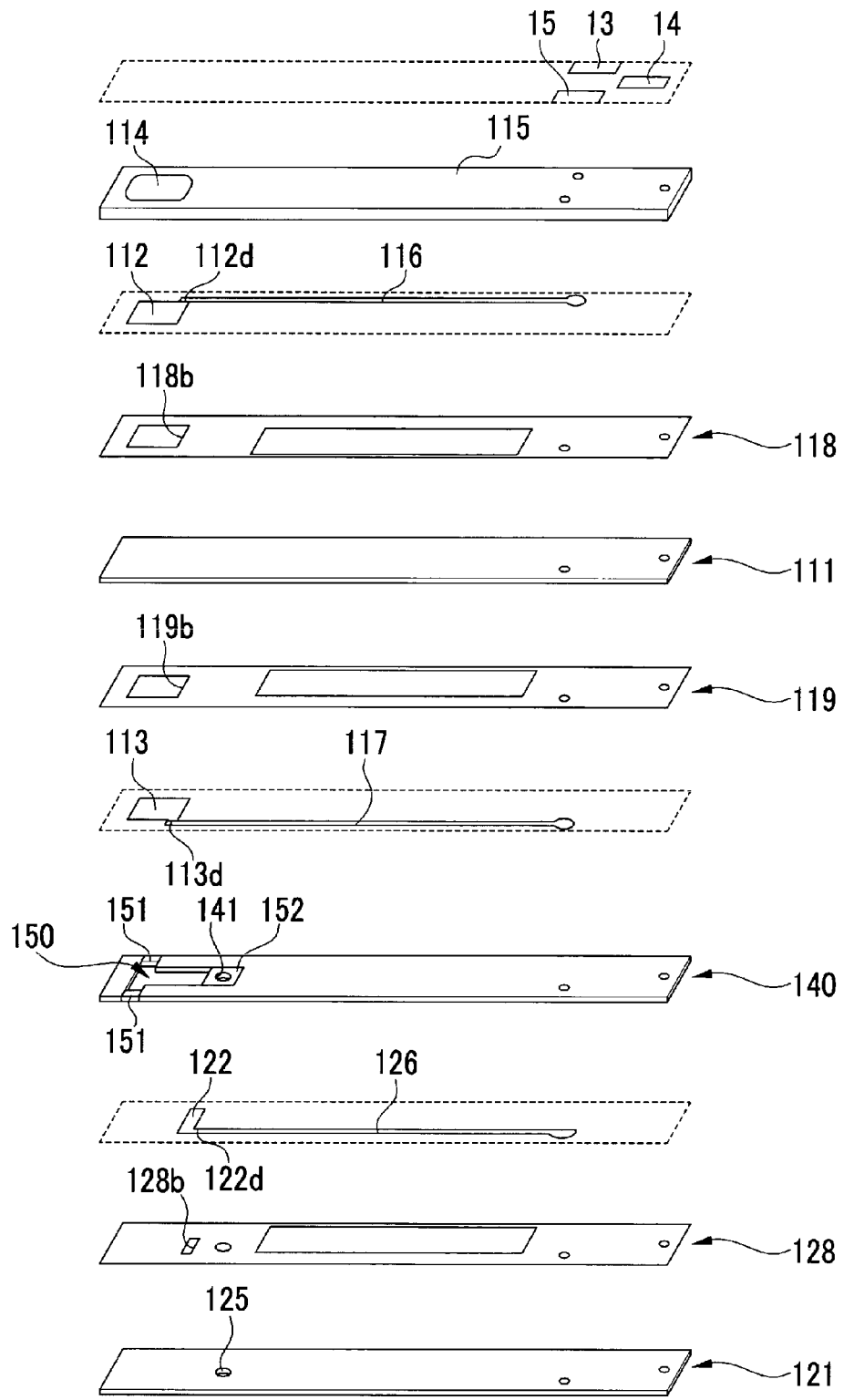
FIG. 5 Enlarged view of region E of FIG. 4.
Figure 6:
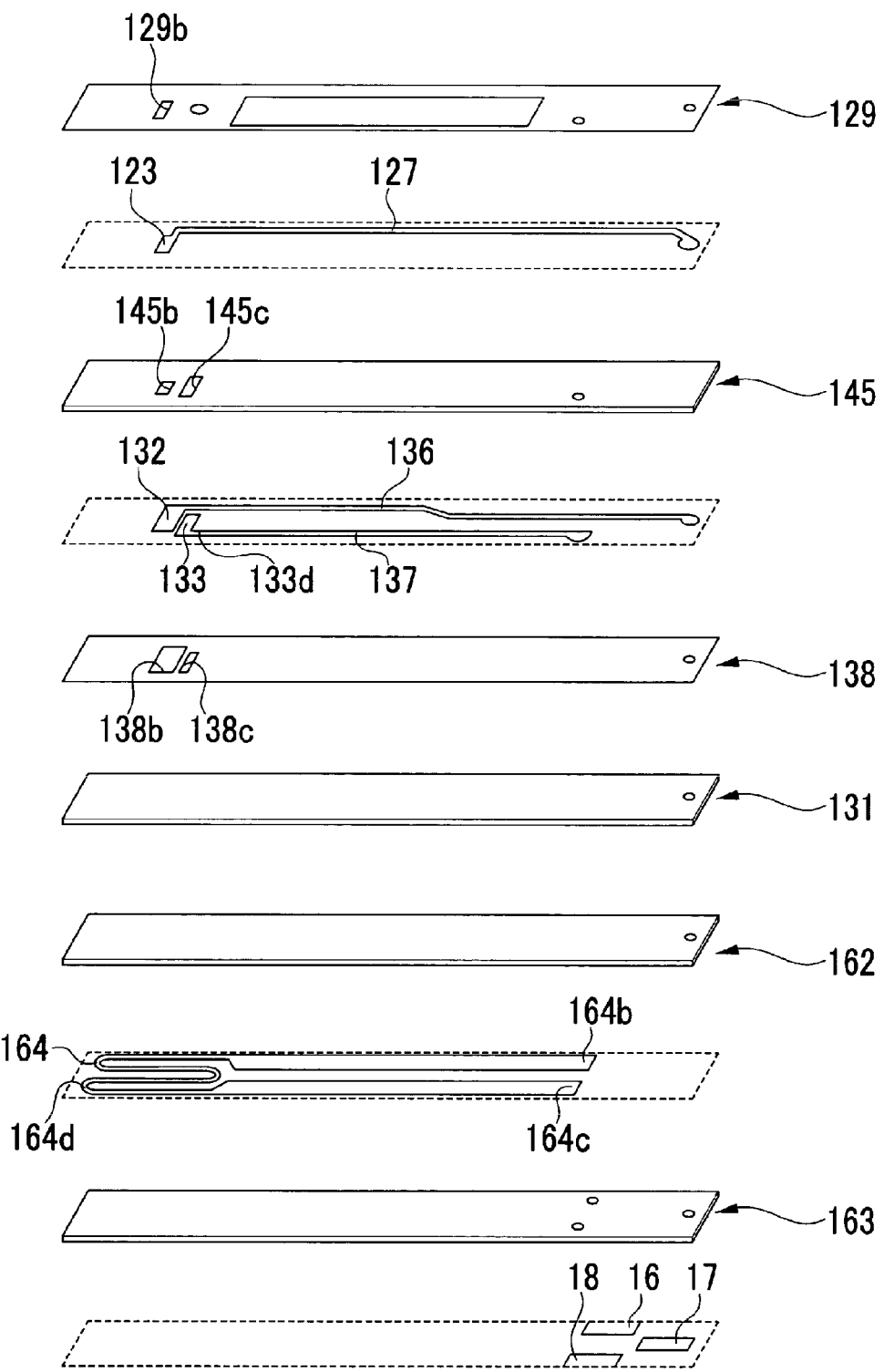
FIG. 6 Enlarged view of region F of FIG. 4.

FIG. 1 is a longitudinal sectional view (sectional view cut along an axial line AX) of a gas sensor 1 according to the present embodiment. FIG. 2 is a perspective view of a gas sensor element 10 according to the present embodiment. FIG. 3 is a sectional view taken along line B-B of FIG. 2, showing an internal structure of the gas sensor element 10. FIG. 4 is a perspective view showing component layers of the gas sensor element 10 in the order of lamination along the direction of lamination (along the vertical direction in FIG. 4). FIG. 5 is an enlarged view of region E of FIG. 4, and FIG. 6 is an enlarged view of region F of FIG. 4.

The gas sensor 1 is a $NO_x$ sensor having the gas sensor element 10 capable of detecting the concentration of $NO_x$ (nitrogen oxide) contained in exhaust gas, which is gas to be measured, and attached, for use, to an exhaust pipe (not shown) of an internal combustion engine (see FIG. 1). The gas sensor 1 includes a tubular metallic shell 20 having a threaded portion 21 formed on its outer surface at a predetermined position for fixing the gas sensor 1 to the exhaust pipe. The gas sensor element 10 has a narrow, elongated plate shape extending in the direction of the axial line AX and is held in the interior of the metallic shell 20 (see FIGS. 1 and 2).

More specifically, the gas sensor 1 includes a holding member 60 having an insertion hole 62 into which a rear end portion 10k (an upper end portion in FIG. 1) of the gas sensor element 10 is inserted, and six terminal members held in the interior of the holding member 60. FIG. 1 shows only two terminal members (specifically, terminal members 75 and 76) out of six terminal members.

A total of six electrode terminals, each having a rectangular shape as viewed in plane, are formed on the rear end portion 10k (a right end portion in FIG. 2) of the gas sensor element 10. Specifically, electrode terminals 13, 14, and 15 are formed on a first surface 10a of the gas sensor element 10, and electrode terminals 16, 17, and 18 are formed on a second surface 10b. The terminal members are in elastic contact with and thus are electrically connected to the electrode terminals 13 to 18, respectively (see FIG. 1). Specifically, element contact portions located at forward end portions of the terminal members are in elastic contact with the electrode terminals 13 to 18, respectively. For example, an element contact portion 75b of the terminal member 75 is in elastic contact with and is thus electrically connected to the electrode terminal 14. Also, an element contact portion 76b of the terminal member 76 is in elastic contact with and thus is electrically connected to the electrode terminal 17 (see FIG. 1).

Furthermore, lead wires 71 are electrically connected to the six terminal members (terminal members 75, 76, etc.), respectively. Specifically, a lead wire crimp portion located at a rear end of each terminal member is crimped to a core wire of the lead wire 71, whereby the lead wire 71 is electrically connected to the terminal member. For example, as shown in FIG. 1, a lead wire crimp portion 77 of the terminal member 75 is crimped to a core wire of the lead wire 71, whereby the lead wire 71 is electrically connected to the terminal member 75. Also, a lead wire crimp portion 78 of the terminal member 76 is crimped to a core wire of another lead wire 71, whereby the lead wire 71 is electrically connected to the terminal member 76.

The metallic shell 20 is a tubular member having a through hole 23 extending therethrough in the direction of the axial line AX. The metallic shell 20 has a ledge 25 protruding radially inward and partially constituting the through hole 23. The metallic shell 20 holds the gas sensor element 10 in the through hole 23 while allowing a forward end portion 10s of the gas sensor element 10 to protrude outward (downward in FIG. 1) from its forward end and allowing a rear end portion 10k of the gas sensor element 10 to protrude outward (upward in FIG. 1) from its rear end.

In the through hole 23 of the metallic shell 20, there are disposed an annular ceramic holder 42, two talc rings 43 and 44 formed by talc powder being charged annularly, and a ceramic sleeve 45. More specifically, the ceramic holder 42, the talc rings 43 and 44, and the ceramic sleeve 45 are stacked in this order from the axially forward side of the metallic shell 20 (the lower side in FIG. 1) to the axially rear side (the upper side in FIG. 1) such that they radially surround the gas sensor element 10.

Also, a metal cup 41 is disposed between the ceramic holder 42 and the ledge 23 of the metallic shell 20. A crimp ring 46 is disposed between the ceramic sleeve 45 and a crimped portion 22 of the metallic shell 20. The crimped portion 22 of the metallic shell 20 is crimped in such a manner as to press forward the ceramic sleeve 45 through the crimp ring 46.

An outer protector 31 and an inner protector 32 which are made of metal (specifically, stainless steel) and have a plurality of holes are welded to a forward end portion 20b of the metallic shell 20 in such a manner as to cover the forward end portion 10s of the gas sensor element 10. Meanwhile, a tubular casing 51 is welded to a rear end portion of the metallic shell 20. The tubular casing 51 extends in the direction of the axial line AX and surrounds the gas sensor element 10.

The holding member 60 is a tubular member formed of an electrically insulating material (specifically, alumina) and having the insertion hole 62 extending therethrough in the direction of the axial line AX. The aforementioned six terminal members (terminal members 75, 76, etc.) are disposed in the insertion hole 62 (see FIG. 1). The holding member 60 has a collar portion 65 formed at its rear end portion and protruding radially outward. The holding member 60 is held by an internal support member 53 in such a manner that the collar portion 65 is in contact with the internal support member 53. The internal support member 53 is held to the tubular housing 51 by means of a crimped portion 51g of the tubular housing 51 being crimped radially inward.

An insulating member 90 is disposed on a rear end surface 61 of the holding member 60. The insulating member 90 is formed of an electrically insulating material (specifically, alumina) and has a cylindrical shape. The insulating member 90 has six through holes 91 extending therethrough in the direction of the axial line AX. The lead wire crimp portions (lead wire crimp portions 77, 78, etc.) of the terminal members are disposed in the through holes 91, respectively.

An elastic seal member 73 formed of fluororubber is disposed radially inward of a rear end opening portion 51c located at an axially rear end portion (an upper end portion in FIG. 1) of the tubular housing 51 (see FIG. 1). The elastic seal member 73 has six cylindrical insertion holes 73c extending therethrough in the direction of the axial line AX. The insertion holes 73c are formed of insertion hole surfaces 73b (cylindrical inner wall surfaces), respectively, of the elastic seal member 73. The lead wires 71 are inserted through the insertion holes 73c in one-to-one relation. The lead wires 71 extend to the outside of the gas sensor 1 through the insertion holes 73c of the elastic seal member 73. The elastic seal member 73 is radially deformed in an elastically compressive manner through radially inward crimping of the rear end opening portion 51c of the tubular housing 51, whereby the insertion hole surfaces 73b and corresponding outer circumferential surfaces 71b of the lead wires 71 are brought into close contact with one another, thereby establishing watertight seal between the insertion hole surfaces 73b and the corresponding outer circumferential surfaces 71b of the lead wires 71.

Meanwhile, as shown in FIG. 3, the gas sensor element 10 includes plate-like solid electrolyte bodies 111, 121, 131 and insulators 140 and 145 disposed between the solid electrolyte bodies 111, 121, and 131 and has a structure in which these members are laminated together in the direction of lamination (vertical direction in FIG. 3). Furthermore, the gas sensor element 10 includes a heater 161 laminated on a back surface 131c (lower surface in FIG. 3) of the solid electrolyte body 131. The heater 161 includes plate-like insulators 162 and 163 formed primarily of alumina and a heater pattern 164 (formed primarily of Pt) embedded between the insulators 162 and 163 (see FIGS. 3 and 6). The heater pattern 164 includes a heat generating portion 164d in a shape resembling the letter W and rectilinear first and second lead portions 164b and 164c connected to opposite ends, respectively, of the heat generating portion 164d. The first lead portion 164b is electrically connected to the electrode terminal 16, and the second lead portion 164c is electrically connected to the electrode terminal 18 (see FIG. 6).

The solid electrolyte bodies 111, 121, and 131 are formed of zirconia, which is solid electrolyte, and has oxygen ion conductivity. A porous Ip1 positive electrode 112 is provided on a front surface 111b (an upper surface in FIG. 3) of the solid electrolyte body 111. A porous Ip1 negative electrode 113 is provided on a back surface 111c (a lower surface in FIG. 3) of the solid electrolyte body 111. The Ip1 positive electrode 112 and the Ip1 negative electrode 113 are formed of cermet which contains Pt powder and ceramic powder, and have oxygen permeability.

In the present embodiment, the Ip1 positive electrode 112 and the Ip1 negative electrode 113 are formed as follows. First, 100 parts by weight Pt powder, 14 parts by weight ceramic powder, and 10 parts by weight organic binder (e.g., ethyl cellulose) are mixed; to the resultant mixture, solvent is added in a predetermined amount, yielding electrode paste. Next, the electrode paste is applied to the front surface 111b and the back surface 111c of the solid electrolyte body 111. Subsequently, the organic binder is dissipated through application of heat, thereby forming the porous electrodes 112 and 113.

As shown in FIG. 5, an Ip1 positive lead 116 is connected to a connection portion 112d of the Ip1 positive electrode 112. The Ip1 positive lead 116 is electrically connected to the electrode terminal 13. An Ip1 negative lead 117 is connected to a connection portion 113d of the Ip1 negative electrode 113. The Ip1 negative lead 117 is electrically connected to the electrode terminal 15. The Ip1 positive lead 116 and the Ip1 negative lead 117 are formed of cermet which contains Pt powder and ceramic powder, but is formed to be dense in contrast to the Ip1 positive electrode 112 and the Ip1 negative electrode 113. Thus, the Ip1 positive lead 116 and the Ip1 negative lead 117 are oxygen-impermeable.

In the present embodiment, the Ip1 positive lead 116 and the Ip1 negative lead 117 are formed as follows. First, 100 parts by weight Pt powder, 18 parts by weight ceramic powder, and 5 parts by weight organic binder (e.g., ethyl cellulose) are mixed; to the resultant mixture, solvent is added in a predetermined amount, yielding lead paste. Next, the lead paste is applied to the front surface 111b and the back surface 111c of the solid electrolyte body 111. Subsequently, the organic binder is dissipated through application of heat, thereby forming the leads 116 and 117.

Meanwhile, as compared with the electrode paste mentioned above, the lead paste is reduced (approximately halved) in the amount of addition of organic binder. Through reduction of the amount of addition of organic binder, which forms internal pores through dissipation thereof as a result of application of heat, the dense leads 116 and 117 having few internal pores are formed.

A protection layer 115 formed of alumina or the like is laminated on the front side (upper side in FIGS. 3 to 5) of the Ip1 positive electrode 112 and the Ip1 positive lead 116. A first porous body 114 is formed in the protection layer 115 at such a position as to face the Ip1 positive electrode 112 in the direction of lamination and is exposed to an ambient atmosphere of the gas sensor element 10. The first porous body 114 has gas permeability and is in contact with a portion of the Ip1 positive electrode 112. That portion of the Ip1 positive electrode 112 which is in contact with the first porous body 114 is a contact portion 112b.

The solid electrolyte body 111 and the electrodes 112 and 113 constitute an Ip1 cell 110 (first pump cell) (see FIG. 3). The Ip1 cell 110 pumps oxygen (so-called oxygen pumping) between an atmosphere in contact with the electrode 112 (ambient atmosphere of the gas sensor element 10) and an atmosphere in contact with the electrode 113 (atmosphere within a first measuring chamber 150, which will be described later) according to pump current Ip1 applied between the electrodes 112 and 113.

The solid electrolyte body 121 is disposed in such a manner as to face the solid electrolyte body 111 in the direction of lamination with the insulator 140 intervening therebetween. A porous Vs negative electrode 122 is provided on a front surface 121b (an upper surface in FIG. 3) of the solid electrolyte body 121. A porous Vs positive electrode 123 is provided on a back surface 121c (a lower surface in FIG. 3) of the solid electrolyte body 121. The Vs negative electrode 122 and the Vs positive electrode 123 are formed of cermet which contains Pt powder and ceramic powder, and have oxygen permeability.

As shown in FIG. 5, a Vs negative lead 126 is connected to a connection portion 122d of the Vs negative electrode 122. The Vs negative lead 126 is electrically connected to the electrode terminal 15. The Vs negative lead 126 is formed of cermet which contains Pt powder and ceramic powder, but is formed to be dense in contrast to the Vs negative electrode 122. Thus, the Vs negative lead 126 is oxygen-impermeable. Meanwhile, as shown in FIGS. 5 and 6, a Vs positive lead 127 is connected to the Vs positive electrode 123. The Vs positive lead 127 is electrically connected to an electrode terminal 14. The Vs positive lead 127 is formed of cermet which contains Pt powder and ceramic powder, but is formed porously, since the Vs positive lead 127 is formed simultaneously with formation of the Vs positive electrode 123. Thus, the Vs positive lead 127 has oxygen permeability.

The first measuring chamber 150, which is an internal space of the gas sensor element, is formed between the solid electrolyte body 111 and the solid electrolyte body 121 (see FIG. 3). The first measuring chamber 150 is an internal space of the gas sensor element 10 into which exhaust gas that flows through an exhaust path is first introduced, and communicates with the ambient atmosphere of the gas sensor element 10 through a second porous body 151 having gas permeability. The second porous body 151 is provided laterally of the first measuring chamber 150 as a partition between the first measuring chamber 150 and the ambient atmosphere of the gas sensor element 10 and limits the amount of inflow per unit time of exhaust gas into the first measuring chamber 150 (see FIGS. 2 and 5).

A third porous body 152 is provided at the rear side (right side in FIG. 3) of the first measuring chamber 150 as a partition between the first measuring chamber 150 and a second measuring chamber 160, which will be described later and limits the amount of flow per unit time of exhaust gas.

The solid electrolyte body 121 and the electrodes 122 and 123 constitute a Vs cell 120 (see FIG. 3). The Vs cell 120 mainly generates electromotive force in response to a difference in partial pressure of oxygen between two atmospheres (an atmosphere within the first measuring chamber 150 in contact with the electrode 122 and an atmosphere within a reference oxygen chamber 170 in contact with the electrode 123) separated by the solid electrolyte body 121.

The solid electrolyte body 131 is disposed in such a manner as to face the solid electrolyte body 121 in the direction of lamination with the insulator 145 sandwiched therebetween. A porous Ip2 positive electrode 132 and a porous Ip2 negative electrode 133 are provided on a front surface 131b (an upper surface in FIG. 3) of the solid electrolyte body 131. The Ip2 positive electrode 132 and the Ip2 negative electrode 133 are formed of cermet which contains Pt powder and ceramic powder, and has oxygen permeability.

As shown in FIG. 6, an Ip2 positive lead 136 is connected to the Ip2 positive electrode 132. The Ip2 positive lead 136 is electrically connected to the electrode terminal 17. The Ip2 positive lead 136 is formed of cermet which contains Pt powder and ceramic powder, but is formed porously, since the Ip2 positive lead 136 is formed simultaneously with formation of the Ip2 positive electrode 132. Thus, the Ip2 positive lead 136 has oxygen permeability. Meanwhile, an Ip2 negative lead 137 is connected to a connection portion 133d of the Ip2 negative electrode 133. The Ip2 negative lead 137 is electrically connected to the electrode terminal 15. The Ip2 negative lead 137 is formed of cermet which contains Pt powder and ceramic powder, but is formed to be dense in contrast to the Ip2 negative electrode 133. Thus, the Ip2 negative lead 137 is oxygen-impermeable.

The reference oxygen chamber 170, which is an isolated small space, is formed at a position in opposition to the Ip2 positive electrode 132; more specifically, between the Ip2 positive electrode 132 and the Vs positive electrode 123 (see FIG. 3). In other words, the Ip2 positive electrode 132 (second electrode) faces (fronts) the reference oxygen chamber 170 formed in the gas sensor element 10. The reference oxygen chamber 170 is an opening 145b formed in the insulator 145. In the reference oxygen chamber 170, a porous body made of ceramic is disposed at a side toward the Ip2 positive electrode 132.

Also, a second measuring chamber 160, which is an internal space of the gas sensor element, is formed at such a position as to face the Ip2 negative electrode 133 in the direction of lamination. In other words, the Ip2 negative electrode 133 (first electrode) faces (fronts) the second measuring chamber 160 formed in the gas sensor element 10. The second measuring chamber 160 is composed of an opening 145c extending through the insulator 145 in the direction of lamination, an opening 125 extending through the solid electrolyte body 121 in the direction of lamination, and an opening 141 extending through the insulator 140 in the direction of lamination.

The first measuring chamber 150 and the second measuring chamber 160 communicate with each other through the third porous body 152 having gas permeability. Therefore, the second measuring chamber 160 communicates with the ambient atmosphere of the gas sensor element 10 through the second porous body 151, the first measuring chamber 150, and the third porous body 152.

In the present embodiment, the solid electrolyte body 131 corresponds to the "solid electrolyte body" appearing in claims. The Ip2 negative electrode 133 corresponds to the "first electrode" appearing in claims. The Ip2 negative lead 137 corresponds to the "first lead" appearing in claims. The Ip2 positive electrode 132 corresponds to the "second electrode" appearing in claims. The second measuring chamber 160 corresponds to the "measuring chamber" appearing in claims. The reference oxygen chamber 170 corresponds to the "destination located externally of the measuring chamber" and the "reference oxygen chamber" appearing in claims. The connection portion 133d corresponds to the "connection portion" appearing in claims.

The solid electrolyte body 131 and the electrodes 132 and 133 constitute an Ip2 cell 130 (second pump cell) for detecting $NO_x$ concentration. The Ip2 cell 130 moves oxygen (oxygen ions) formed through decomposition of $NO_x$ decomposed in the second measuring chamber 160, to a destination located externally of the second measuring chamber 160; i.e., to the reference oxygen chamber 170, through the solid electrolyte body 131. At this time, an electric current corresponding to the concentration of $NO_x$ contained in exhaust gas (gas to be measured) introduced into the second measuring chamber 160 flows through the lead 136 connected to the electrode 132 and through the lead 137 connected to the electrode 133.

In the present embodiment, an alumina insulation layer 138 is formed on the front surface 131b of the solid electrolyte body 131. Furthermore, the Ip2 positive lead 136 and a portion of the Ip2 positive electrode 132 are formed on the alumina insulation layer 138. Furthermore, the Ip2 negative lead 137 and a portion of the Ip2 negative electrode 133 are formed on the alumina insulation layer 138 (and are thus in noncontact with the electrolyte body 131). Also, the connection portion 133d of the Ip2 negative electrode 133 is connected to the lead 137 on the alumina insulation layer 138. The connection portion 133d is located externally of the second measuring chamber 160 and is a portion of the Ip2 negative electrode 133 located most distant from the second measuring chamber 160 (see FIG. 7).

The electrode 132 has a contact portion 132c which is in contact with the solid electrolyte body 131 through a through hole 138b extending through the alumina insulation layer 138 in the direction of lamination. An exposure portion 133b of the electrode 133 exposed to the second measuring chamber 160 has a contact portion 133c which is in contact with the solid electrolyte body 131 through a through hole 138c extending through the alumina insulation layer 138 in the direction of lamination (see FIG. 3).

Therefore, in the present embodiment, the connection portion 133d of the Ip2 negative electrode 133 is disposed at a position not exposed to the second measuring chamber 160 and is in noncontact with the solid electrolyte body 131. Thus, only the contact portion 133c of the Ip2 negative electrode 133 can actually function as a sensing portion, and an object of detection; i.e., $NO_x$ concentration, can be accurately detected. The lead 137 differs from the electrode 133 in electrical characteristics; therefore, a configuration in which the lead and the connection portion connected to the lead are partially in contact with the solid electrolyte body is inferior, in accuracy in detecting gas concentration, to the present embodiment in which such contact is not involved.

In the present embodiment, the exposure portion 133*b* corresponds to the "exposure portion" appearing in claims. The alumina insulation layer 138 corresponds to the "insulation layer" appearing in claims. The contact portion 133*c* corresponds to the "contact portion" appearing in claims.

In the present embodiment, an alumina insulation layer 118 is formed on the front surface 111*b* of the solid electrolyte body 111 (see FIG. 3). Furthermore, the Ip1 positive lead 116 and a portion of the Ip1 positive electrode 112 are formed on the alumina insulation layer 118. Furthermore, the contact portion 112*b* of the Ip1 positive electrode 112 has a contact portion 112*c* which is in contact with the solid electrolyte body 111 through a through hole 118*b* extending through the alumina insulation layer 118 in the direction of lamination.

Furthermore, an alumina insulation layer 119 is formed on the back surface 111*c* of the solid electrolyte body 111. Also, the Ip1 negative lead 117 and a portion of the Ip1 negative electrode 113 are formed on the alumina insulation layer 119. Furthermore, that exposure portion 113*b* of the Ip1 negative electrode 113 which is exposed to the first measuring chamber 150 has a contact portion 113*c* which is in contact with the solid electrolyte body 111 through a through hole 119*b* extending through the alumina insulation layer 119 in the direction of lamination.

Furthermore, in the present embodiment, an alumina insulation layer 128 is formed on the front surface 121*b* of the solid electrolyte body 121. Also, the Vs negative lead 126 and a portion of the Vs negative electrode 122 are formed on the alumina insulation layer 128. Furthermore, that exposure portion 122*b* of the Vs negative electrode 122 which is exposed to the first measuring chamber 150 has a contact portion 122*c* which is in contact with the solid electrolyte body 121 through a through hole 128*b* extending through the alumina insulation layer 128 in the direction of lamination.

Furthermore, an alumina insulation layer 129 is formed on the back surface 121*c* of the solid electrolyte body 121. Also, the Vs positive lead 127 and a portion of the Vs positive electrode 123 are formed on the alumina insulation layer 129. Furthermore, the Vs positive electrode 123 has a contact portion 123*c* which is in contact with the solid electrolyte body 121 through a through hole 129*b* extending through the alumina insulation layer 129 in the direction of lamination.

Figure 7:
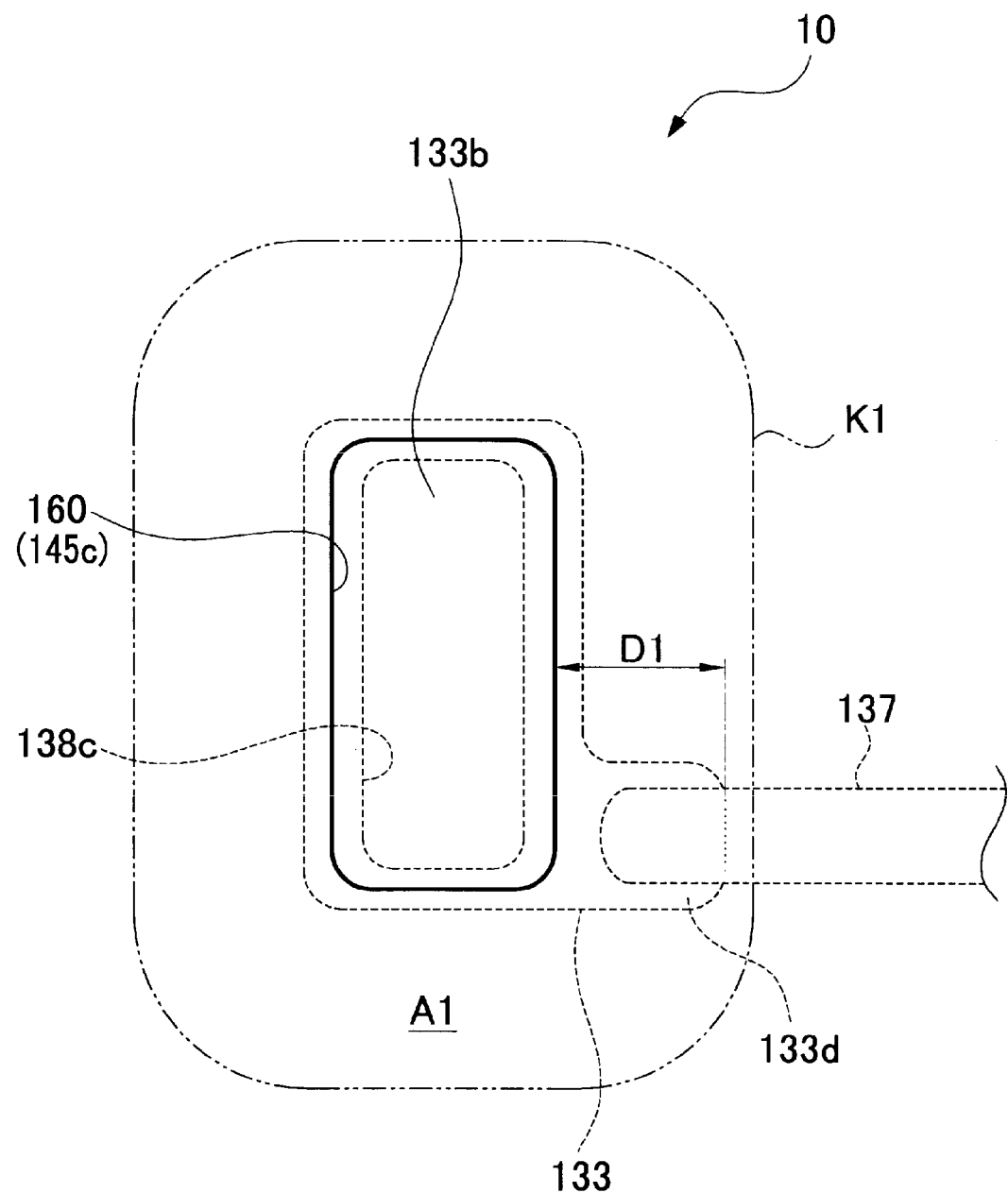
FIG. 7 View showing the position of a connection portion of an Ip2 negative electrode as viewed in the direction of arrow C of FIG. 3.

Also, in the present embodiment, the connection portion 133*d* of the Ip2 negative electrode 133 is disposed at a position not exposed to the second measuring chamber 160 and is connected to the Ip2 negative lead 137 at a position located externally of the second measuring chamber 160 (see FIG. 7). Thus, in contrast to the invention of Patent Document 1 (Japanese Patent No. 4165652) mentioned above, there can be restrained "deterioration in accuracy in detecting the concentration of $NO_x$ in gas to be measured, as a result of deterioration in oxygen pumping performance stemming from disposition of the connection portion within the measuring chamber."

Detection of $NO_x$ concentration by the gas sensor 1 of the present embodiment will be described briefly.

As the heater pattern 164 rises in temperature, the solid electrolyte bodies 111, 121, and 131 of the gas sensor element 10 are heated and thus activated. This initiates operation of the Ip1 cell 110, the Vs cell 120, and the Ip2 cell 130.

Before starting regular control for detecting the concentration of $NO_x$ in exhaust gas (gas to be measured), the following control is performed: a fixed current is applied between the electrode 132 and the electrode 133 for a fixed period of time (e.g., 20 seconds) for moving (pumping out) oxygen stagnating in the interior of the gas sensor element 10 to the reference oxygen chamber 170 through the second measuring chamber 160. The reason for performing such control is to properly detect the concentration of $NO_x$ (the concentration of oxygen stemming from $NO_x$) in gas-to-be-measured introduced from outside without influence of oxygen stagnating in the interior of the gas sensor element 10 (more specifically, in the interior of the second measuring chamber 160 and the electrode 133).

Exhaust gas (gas to be measured) which flows through an exhaust path (not shown) is introduced into the first measuring chamber 150 while being limited in flow rate by the second porous body 151. At this time, a weak current Icp is applied to the Vs cell 120 and flows from the electrode 123 to the electrode 122. Thus, oxygen contained in exhaust gas can receive electrons from the electrode 122, which is a negative electrode, within the first measuring chamber 150 and become oxygen ions; and the oxygen ions flow through the solid electrolyte body 121 and move into the reference oxygen chamber 170. That is, as a result of application of the current Icp between the electrodes 122 and 123, oxygen in the first measuring chamber 150 is sent to the reference oxygen chamber 170.

In the case where the oxygen concentration of exhaust gas introduced into the first measuring chamber 150 is lower than a predetermined value, the current Ip1 is applied to the Ip1 cell 110 in such a manner that the electrode 112 becomes a negative electrode, so as to pump oxygen into the first measuring chamber 150 from the ambient atmosphere of the gas sensor element 10. By contrast, in the case where the oxygen concentration of exhaust gas introduced into the first measuring chamber 150 is higher than the predetermined value, the current Ip1 is applied to the Ip1 cell 110 in such a manner that the electrode 113 becomes a negative electrode, so as to pump out oxygen from inside the first measuring chamber 150 to the ambient atmosphere of the gas sensor element 10.

Exhaust gas whose oxygen concentration has been adjusted as mentioned above in the first measuring chamber 150 is introduced into the second measuring chamber 160 through the third porous body 152. $NO_x$ contained in exhaust gas comes into contact with the electrode 133 within the second measuring chamber 160 and is decomposed (reduced) on the electrode 133 into nitrogen and oxygen through application of the fixed voltage Vp2 between the electrodes 132 and 133; and oxygen generated through the decomposition flows, in the form of oxygen ions, through the solid electrolyte body 131 and moves into the reference oxygen chamber 170. At this time, residual oxygen which has not been pumped out from the first measuring chamber 150 similarly moves into the reference oxygen chamber 170 through operation of the Ip2 cell 130. Thus, current stemming from $NO_x$ and current stemming from residual oxygen flow through the Ip2 cell 130.

Since residual oxygen which has not been pumped out from the first measuring chamber 150 is adjusted in concentration to the predetermined value as mentioned above, current stemming from the residual oxygen can be considered substantially constant and thus has little influence on variation in current stemming from $NO_x$; thus, current flowing through the Ip2 cell 130 is proportional to $NO_x$ concentration. Therefore, by means of detecting the current Ip2 which flows through the Ip2 cell 130, the concentration of $NO_x$ in exhaust gas can be detected on the basis of the detected current Ip2.

In the gas sensor 1 of the present embodiment, as mentioned above, the gas sensor element 10 includes the oxygen-permeable Ip2 negative electrode 133 and the oxygen-impermeable Ip2 negative lead 137 connected to the Ip2 negative electrode 133. The electrode 133 has the exposure portion 133b exposed to the second measuring chamber 160, and the connection portion 133d connected to the lead 137 and disposed at a position not exposed to the second measuring chamber 160. For connection to the lead 137 at a position located externally of the second measuring chamber 160, the connection portion 133d is formed through extension of the electrode 133 in a direction directed away from the second measuring chamber 160; thus, the connection portion 133d is a portion of the electrode 133 located most distant from the second measuring chamber 160 (see FIG. 7).

Conventionally, a thus-configured gas sensor element has involved risk of failure to quickly pump out oxygen stagnating in the connection portion of the Ip2 negative electrode. Thus, risk of occurrence of the following phenomenon has been involved: even after start of regular control for detecting the concentration of $NO_x$ in gas to be measured, much oxygen remains within (adsorbs to) the connection portion, and, during regular control, the residual oxygen moves into the measuring chamber little by little over time. Because of influence of such supply of the residual oxygen from the connection portion into the measuring chamber over a long period of time, there has been involved risk of consumption of a long period of time from start of control until stabilization of sensor outputs (current flowing between the electrode 132 and the electrode 133 as a result of movement of oxygen ions from the second measuring chamber 160 to the reference oxygen chamber 170 through the solid electrolyte body 131, and $NO_x$ concentration corresponding to the current). That is, there has been involved risk of consumption of a long period of time until establishment of a condition in which the concentration of $NO_x$ in gas to be measured can be properly detected.

By contrast, in the gas sensor element 10 of the gas sensor 1 of the present embodiment, as shown in FIG. 7, the entirety of the connection portion 133d of the Ip2 negative electrode 133 is disposed inside a region A1 (surrounded by the dash-dot-dot line K1 in FIG. 7) which extends from the second measuring chamber 160 over a distance of 1.0 mm or less. By virtue of this, oxygen stagnating in the connection portion 133d can be quickly pumped out, whereby there can be reduced time from start of control of the gas sensor 1 (gas sensor element 10) until stabilization of sensor output. That is, in a short period of time, there can be established a condition in which the concentration of $NO_x$ in gas to be measured can be properly detected. This is apparent from the results of a performance evaluation test, which will be described later.

Modified Embodiment

Next, a modified embodiment of the present invention will be described. A gas sensor 201 of the modified embodiment differs from the gas sensor 1 of the embodiment only in the gas sensor element and is similar in other features (see FIG. 1). More specifically, a gas sensor element 210 of the present modified embodiment differs from the gas sensor element 10 of the embodiment in the position of the Ip2 negative electrode in relation to the second measuring chamber and is substantially similar in other features. Therefore, features different from those of the embodiment will be described, and description of similar features will be omitted or simplified.

In the gas sensor element 10 of the embodiment, as shown in FIG. 7, the connection portion 133d of the Ip2 negative electrode 133 is disposed inside the region A1 (surrounded by the dash-dot-dot line K1 in FIG. 7) which extends from the second measuring chamber 160 over a distance of 1.0 mm or less.

Figure 10:
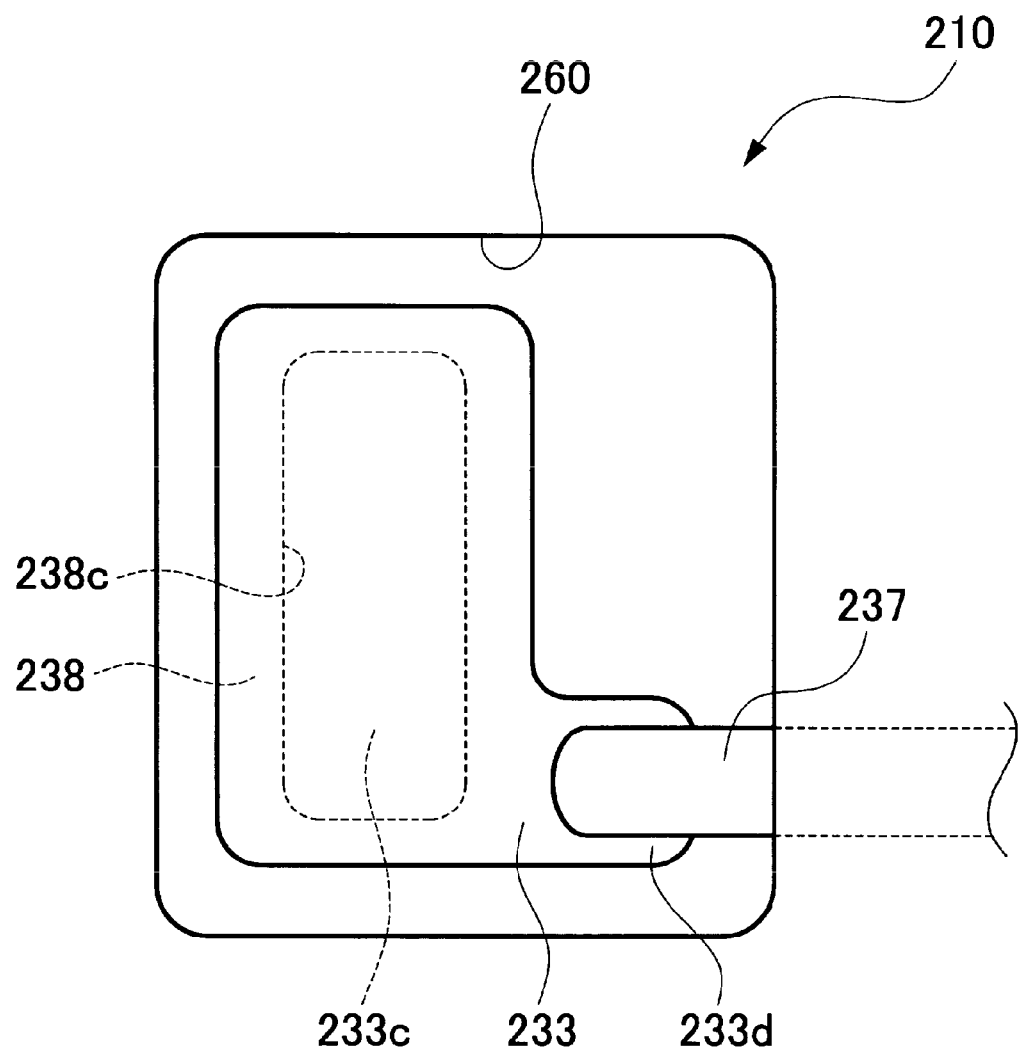
FIG. 10 View showing the position of a connection portion of an Ip2 negative electrode of a gas sensor element according to a modified embodiment.

By contrast, in the gas sensor element 210 of the present modified embodiment, as shown in FIG. 10, an Ip2 negative electrode 233 is disposed within a second measuring chamber 260. That is, the entirety of the Ip2 negative electrode 233 including a connection portion 233d is disposed within the second measuring chamber 260. Thus, the entirety of the Ip2 negative electrode 233 including the connection portion 233d is exposed to the second measuring chamber 260. Also, an Ip2 negative lead 237 is connected to the connection portion 233d of the Ip2 negative electrode 233 at a position within the second measuring chamber 260.

Through employment of such a configuration, oxygen stagnating in the connection portion 233d of the Ip2 negative electrode 233 can be quickly pumped out, whereby there can be reduced time from start of control until stabilization of sensor output. That is, in a short period of time, there can be established a condition in which the concentration of $NO_x$ in gas to be measured can be properly detected. This is apparent from the results of the performance evaluation test, which will be described later.

An alumina insulation layer 238 is formed on the front surface 131b of the solid electrolyte body 131, and the Ip2 negative electrode 233 has a contact portion 233c which is in contact with the solid electrolyte body 131 through a through hole 238c in the alumina insulation layer 238 (see FIG. 10). Meanwhile, the Ip2 negative lead 237 is formed on the alumina insulation layer 238 (and is thus in noncontact with the solid electrolyte body 131). The connection portion 233d of the Ip2 negative electrode 233 is connected to the Ip2 negative lead 237 on the alumina insulation layer 238 (and is thus in noncontact with the solid electrolyte body 131).

Therefore, although the connection portion 233d is disposed within the second measuring chamber 260, the connection portion 233d does not affect oxygen pumping performance of the Ip2 negative electrode 233 (the connection portion 233d does not cause deterioration in oxygen pumping performance of the Ip2 negative electrode 233). Thus, there can be restrained deterioration in accuracy in detecting the concentration of $NO_x$ in gas to be measured. Furthermore, only the contact portion 233c of the Ip2 negative electrode 233 can actually function as a sensing portion; thus, an object of detection; i.e., $NO_x$ concentration, can be accurately detected.

In the present modified embodiment, the Ip2 negative electrode 233 corresponds to the "first electrode" appearing in claims. The connection portion 233d corresponds to the "connection portion" appearing in claims. The Ip2 negative lead 237 corresponds to the "first lead" appearing in claims. The alumina insulation layer 238 corresponds to the "insulation layer" appearing in claims. The contact portion 233c corresponds to the "contact portion" appearing in claims.

Performance Evaluation Test

Next will be described a performance evaluation test conducted on gas sensor elements (gas sensors).

First, there were fabricated gas sensor elements which differed in distance D1 (see FIG. 7) between the second measuring chamber and that portion of the connection portion of the Ip2 negative electrode which is located most distant from the second measuring chamber. The distance D1 was varied from 0 mm to 2.0 mm at 0.5 mm intervals. Next, gas sensors (see FIG. 1) were fabricated by use of the gas sensor elements. In this manner, the gas sensors which differed in distance D1 were prepared. The gas sensor element having a distance D1 of 0 mm corresponds to the gas sensor element 210 of the modified embodiment and is configured such that the entirety of the Ip2 negative electrode 233 including the connection portion 233d is disposed within the second measuring chamber 260.

Next, the performance evaluation test was conducted on the gas sensors while using the atmosphere (air) as gas to be measured. Specifically, after activation of the solid electrolyte bodies of the gas sensors, the gas sensors were controlled, and the concentration of $NO_x$ in the gas to be measured was measured. First, control is performed so as to apply a fixed current between the electrodes 132 and 133 for a fixed period of time (e.g., 20 seconds), thereby moving (pumping out) oxygen stagnating in the gas sensor elements to the reference oxygen chambers 170 through the second measuring chambers 160. In the present specification, this control is called preliminary control.

Subsequently, a fixed voltage Vp2 is applied between the electrodes 132 and 133, thereby performing regular control for detecting the concentration of $NO_x$ in the gas to be measured. Through application of the fixed voltage Vp2 between the electrodes 132 and 133, $NO_x$ which is contained in the gas to be measured and comes into contact with the electrodes 133 within the second measuring chambers 160 is decomposed (reduced) on the electrodes 133 into nitrogen and oxygen, and oxygen generated through the decomposition flows, in the form of oxygen ions, through the solid electrolyte bodies 131 and moves into the reference oxygen chambers 170. Accordingly, current stemming from $NO_x$ flows through the Ip2 cells 130.

Figure 8:
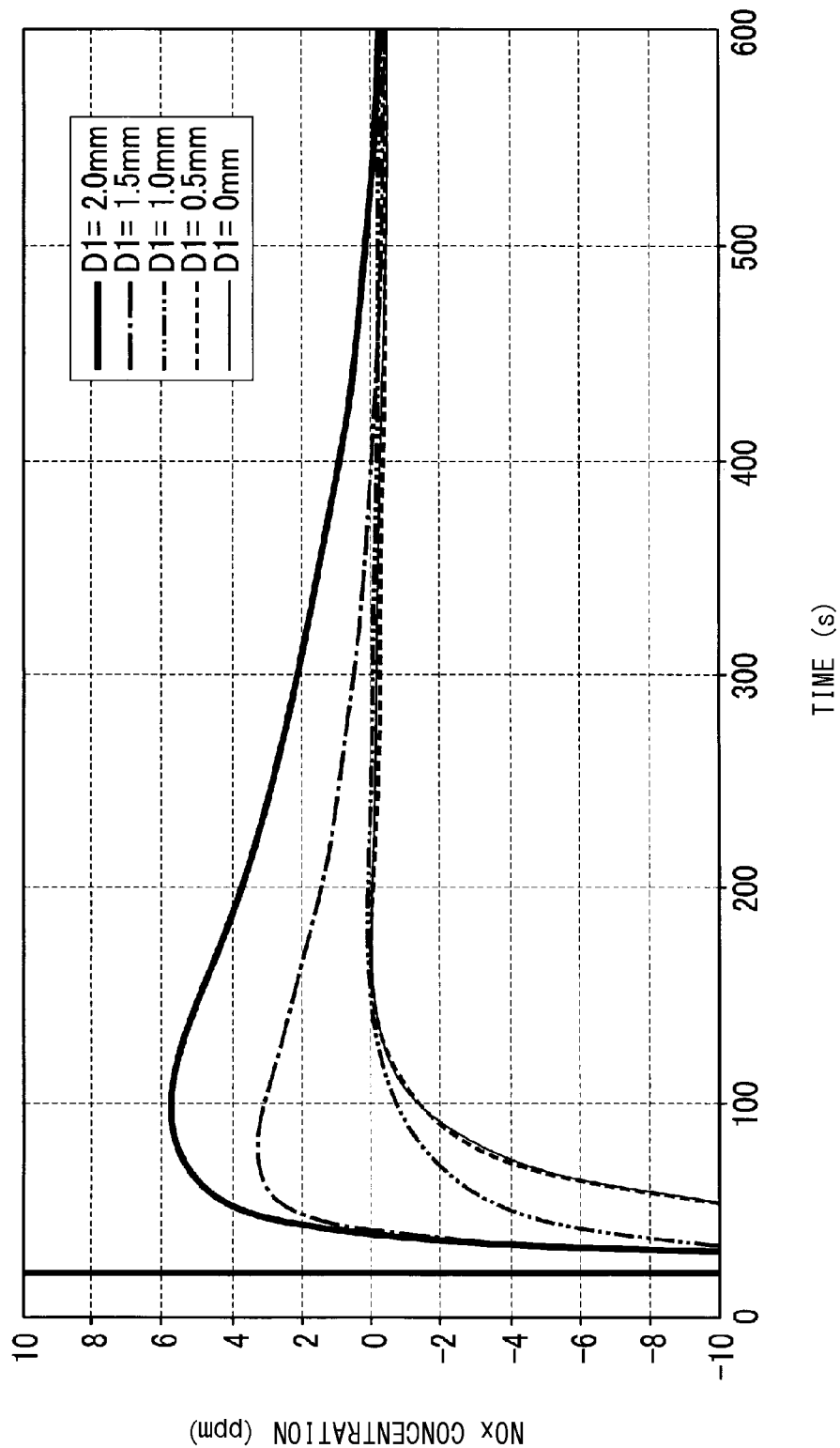
FIG. 8 Graph showing the results of a performance evaluation test conducted on gas sensor elements.

In the present test conducted on the gas sensors, there was detected the current Ip2 which flowed through the Ip2 cells 130 from start of control (preliminary control), and, on the basis of the detected current, a concentration (ppm) of $NO_x$ in the gas to be measured was measured. FIG. 8 shows the results of the test. Since the present test employs the atmosphere (air) as gas to be measured, when the $NO_x$ concentration is stabilized at a value near 0 ppm, stabilization of output is established; that is, it can be determined that there has been established a condition in which the concentration of $NO_x$ in the gas to be measured can be properly detected.

In FIG. 8, the thin line represents data on the gas sensor having a distance D1 of 0 mm. The broken line represents data on the gas sensor having a distance D1 of 0.5 mm. The dash-dot-dot line represents data on the gas sensor having a distance D1 of 1.0 mm. The dash-dot line represents data on the gas sensor having a distance D1 of 1.5 mm. The bold line represents data on the gas sensor having a distance D1 of 2.0 mm.

Figure 9:
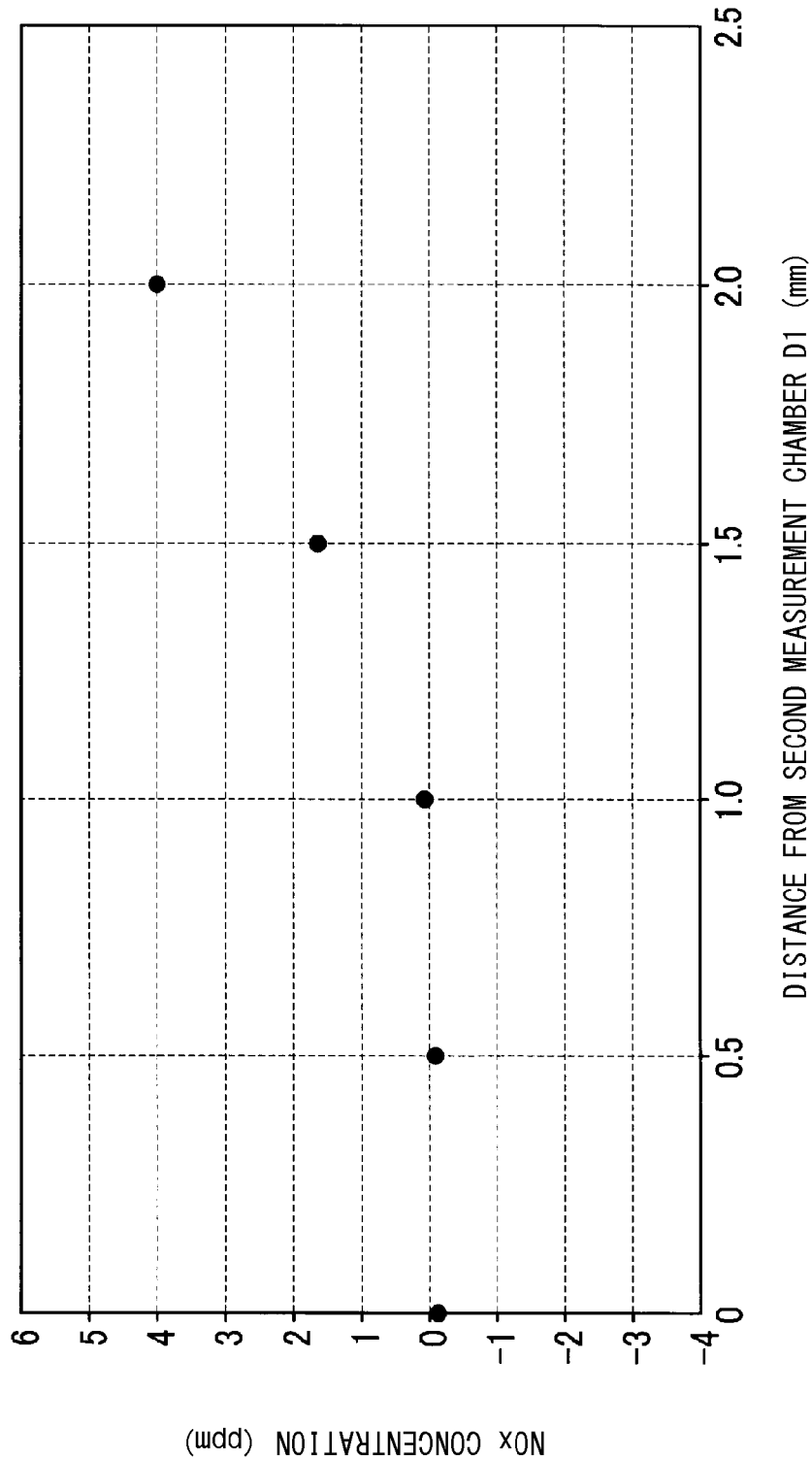
FIG. 9 Another graph showing the results of the performance evaluation test conducted on gas sensor elements.

$NO_x$ concentration was detected 180 seconds after start of control for the gas sensors. FIG. 9 shows the results of the detection. FIG. 9 shows $NO_x$ concentration with the distance D1.

As shown in FIG. 8, at a distance D1 of greater than 1.0 mm, a long period of time was required until $NO_x$ concentration stabilized at around 0 ppm. Specifically, at a distance D1 of 1.5 mm, a time of about 400 seconds was required until $NO_x$ concentration stabilized at around 0 ppm. $NO_x$ concentration detected 180 seconds after start of control was about 1.8 ppm (see FIG. 9). At a distance D1 of 2.0 mm, a time of about 600 seconds was required until $NO_x$ concentration stabilized at around 0 ppm. $NO_x$ concentration detected 180 seconds after start of control was about 4.0 ppm (see FIG. 9).

At a distance D1 of greater than 1.0 mm, as mentioned above, a long period of time was required until stabilization of output, conceivably, for the following reason. At a distance D1 of greater than 1.0 mm, conceivably, even though preliminary control is performed, oxygen stagnating in the connection portion of the Ip2 negative electrode cannot be quickly pumped out. Accordingly, conceivably, even after start of regular control for detecting the concentration of $NO_x$ in gas to be measured, the following phenomenon arises: much oxygen remains in (adsorbs to) the connection portion, and, during regular control, the residual oxygen moves little by little into the second measuring chamber. As a result, a long period of time is required until stabilization of sensor output from start of control; i.e., until establishment of a condition in which the concentration of $NO_x$ in gas to be measured can be properly detected.

By contrast, as shown in FIG. 8, at a distance D1 of 1.0 mm or less, $NO_x$ concentration stabilized at around 0 ppm about 180 seconds after start of control. Also, as shown in FIG. 9, at a distance D1 of 1.0 mm or less, $NO_x$ concentration detected 180 seconds after start of control was about 0 ppm.

As is apparent from the above-mentioned results of the test, through employment of a distance D1 of 1.0 mm or less, oxygen stagnating in the connection portion 133d can be quickly pumped out, whereby there can be reduced time from start of control until stabilization of output. That is, in a short period of time, there can be established a condition in which the concentration of $NO_x$ in gas to be measured can be properly detected.

While the present invention has been described with reference to the embodiment and the modified embodiment, the present invention is not limited thereto, but may be modified as appropriate without departing from the gist of the invention.

For example, the embodiment and the modified embodiment are described while referring to the gas sensor in which the reference oxygen chamber 170 is a destination of oxygen (oxygen ions) generated through decomposition of $NO_x$ in the second measuring chamber 160. However, the present invention is not limited to such a gas sensor, but can be applied to a gas sensor in which a destination of oxygen (oxygen ions) generated through decomposition of $NO_x$ in the second measuring chamber 160 is a space being different from the reference oxygen chamber 170 and located externally of the second measuring chamber 160 (e.g., the first measuring chamber 150, a space which is located externally of the gas sensor element 10 and in which gas to be measured flows, or a space which is located externally of the gas sensor element 10 and in which the air flows).

DESCRIPTION OF REFERENCE NUMERALS 1, 201: gas sensor
10, 210: gas sensor element
111, 121, 131: solid electrolyte body
111b, 121b, 131b: front surface of solid electrolyte body
111c, 121c, 131c: back surface of solid electrolyte body
132: Ip2 positive electrode (second electrode)
133, 233: Ip2 negative electrode (first electrode)

133b: exposure portion
133c, 233c: contact portion
133d, 233d: connection portion
136: Ip2 positive lead
137, 237: Ip2 negative lead (first lead)
138, 238: alumina insulation layer (insulation layer)
138c, 238c: through hole
150: first measuring chamber
160, 260: second measuring chamber (measuring chamber)
170: reference oxygen chamber
A1: region which extends from second measuring chamber (measuring chamber) over a distance of 1.0 mm or less

The invention claimed is:

1. A gas sensor element comprising:
a plate-like first solid electrolyte body having oxygen ion conductivity;
an oxygen-permeable first electrode provided on a front or back surface of the first solid electrolyte body;
an oxygen-impermeable first lead connected to the first electrode;
an oxygen-permeable second electrode provided on the front or back surface of the first solid electrolyte body; and
a first measuring chamber which is disposed in opposition to the first electrode and into which gas to be measured is introduced; and
configured such that oxygen ions stemming from NOx contained in the gas-to-be-measured introduced into the first measuring chamber move from the first measuring chamber to a destination located externally of the measuring chamber through the first solid electrolyte body, whereby a current corresponding to the concentration of oxygen stemming from the NOx flows between the first electrode and the second electrode; wherein
the first electrode has an exposure portion exposed to the first measuring chamber, and a connection portion which is disposed at a position not exposed to the first measuring chamber and is connected to the first lead and which is a portion of the first electrode located most distant from the first measuring chamber, and
the entire connection portion is located in a region which extends from the first measuring chamber over a distance of 1.0 mm or less.

2. A gas sensor element as claimed in claim 1, further comprising a reference oxygen chamber disposed in opposition to the second electrode, wherein the destination located externally of the first measuring chamber is the reference oxygen chamber.

3. A gas sensor element as claimed in claim 1, further comprising an insulation layer formed on the front or back surface of the first solid electrolyte body, wherein
the first lead and a portion of the first electrode are formed on the insulation layer;
the exposure portion of the first electrode includes a contact portion which is in contact with the solid electrolyte body through a through hole extending through the insulation layer; and
the connection portion of the first electrode is connected to the first lead on the insulation layer.

4. A gas sensor element comprising:
a plate-like first solid electrolyte body having oxygen ion conductivity;
an oxygen-permeable first electrode provided on a front or back surface of the first solid electrolyte body;
an oxygen-impermeable first lead connected to the first electrode;
an oxygen-permeable second electrode provided on the front or back surface of the first solid electrolyte body; and
a first measuring chamber which is disposed in opposition to the first electrode and into which gas to be measured is introduced; and
configured such that oxygen ions stemming from NOx contained in the gas-to-be-measured introduced into the first measuring chamber move from the first measuring chamber to a destination located externally of the first measuring chamber through the first solid electrolyte body, whereby a current corresponding to the concentration of oxygen stemming from the NOx flows between the first electrode and the second electrode; wherein
the first electrode is disposed within the first measuring chamber;
the gas sensor element further comprises an insulation layer formed on the front or back surface of the first solid electrolyte body;
the first lead and a portion of the first electrode are formed on the insulation layer;
the first electrode has a contact portion which is in contact with the first solid electrolyte body through a through hole extending through the insulation layer, and a connection portion connected to the first lead on the insulation layer within the measuring chamber;
the first electrode is directly provided on the first solid electrolyte body;
the first lead is electrically connected to the first electrode;
the second electrode is directly provided on the first solid electrolyte body; and
the first lead and the first electrode are both provided on the same surface.

5. A gas sensor element as claimed in claim 4, further comprising a reference oxygen chamber disposed in opposition to the second electrode, wherein the destination located externally of the first measuring chamber is the reference oxygen chamber.

6. A gas sensor comprising a gas sensor element as claimed in claim 1.

7. A gas sensor comprising a gas sensor element as claimed in claim 4.

8. A gas sensor element as claimed in claim 1, further comprising a second measuring chamber and an oxygen pumping cell, the oxygen pumping cell is arranged above and on a side of the first measuring chamber that is opposite the first solid electrolyte body, the oxygen pumping cell is constituted by a second solid electrolyte body and third and fourth electrodes arranged on opposite surfaces of the second solid electrolyte body, the second measuring chamber is arranged below the first measuring chamber, one of said third and fourth electrodes is exposed to the second measuring chamber, and a part of the first measuring chamber is contiguous with the first solid electrolyte body having thereon the first and second electrodes.

9. A gas sensor element as claimed in claim 4, further comprising a second measuring chamber and an oxygen pumping cell, the oxygen pumping cell is arranged above and on a side of the first measuring chamber that is opposite the first solid electrolyte body, the oxygen pumping cell is constituted by a second solid electrolyte body and third and fourth electrodes arranged on opposite surfaces of the second solid electrolyte body, the second measuring chamber is arranged below the first measuring chamber, one of said third and fourth electrodes is exposed to the second measuring chamber, and a part of the first measuring chamber is contiguous with the first solid electrolyte body having thereon the first and second electrodes.

* * * * *